(12) United States Patent
Kemp

(10) Patent No.: US 11,253,332 B1
(45) Date of Patent: Feb. 22, 2022

(54) SHARPS CONTAINER WITH BLACKOUT STRIP

(71) Applicant: Elizabeth Kemp, Oconomowoc, WI (US)

(72) Inventor: Elizabeth Kemp, Oconomowoc, WI (US)

( * ) Notice: Subject to any disclaimer, the term of this patent is extended or adjusted under 35 U.S.C. 154(b) by 120 days.

(21) Appl. No.: 16/686,919

(22) Filed: Nov. 18, 2019

(51) Int. Cl.
| | |
|---|---|
| *B65D 83/10* | (2006.01) |
| *A61B 50/36* | (2016.01) |
| *A61M 5/32* | (2006.01) |
| *B65F 1/16* | (2006.01) |
| *A61B 50/00* | (2016.01) |

(52) U.S. Cl.
CPC ......... *A61B 50/362* (2016.02); *A61M 5/3205* (2013.01); *A61B 2050/006* (2016.02); *A61B 2050/0056* (2016.02); *A61B 2050/0089* (2016.02); *B65F 1/1607* (2013.01); *B65F 1/1615* (2013.01)

(58) Field of Classification Search
CPC ............ A61B 50/362; A61B 17/06114; A61B 2050/0056; A61B 2050/006; A61M 5/3205; B65F 1/1607; B65F 1/1615
USPC ..... 206/363–366, 370, 459.1, 459.5; 40/310, 40/312; 340/568.1; 588/260
See application file for complete search history.

(56) References Cited

U.S. PATENT DOCUMENTS

| | | | | |
|---|---|---|---|---|
| 4,989,307 A | * | 2/1991 | Sharpe | A61M 5/3205 128/917 |
| 5,918,739 A | * | 7/1999 | Bilof | A61B 50/362 206/366 |
| 7,124,680 B2 | * | 10/2006 | Poss | B65F 1/1405 100/229 A |
| 7,971,715 B1 | * | 7/2011 | Fernandes | A61B 50/362 206/366 |
| 2006/0265241 A1 | * | 11/2006 | Mallett | A61B 90/98 206/366 |
| 2011/0248041 A1 | * | 10/2011 | Dooley | A47F 1/065 221/1 |
| 2013/0075295 A1 | * | 3/2013 | Sina | B65D 43/0208 206/459.5 |
| 2013/0306507 A1 | * | 11/2013 | Sichau | A61B 50/39 206/366 |
| 2014/0374294 A1 | * | 12/2014 | Joyce | G16H 20/10 206/363 |

\* cited by examiner

*Primary Examiner* — Luan K Bui
(74) *Attorney, Agent, or Firm* — Donald J. Ersler

(57) ABSTRACT

A sharps container includes a container portion and a closeable lid. The sharps container includes any suitable cross-sectional shape having at least one wall. The container portion is fabricated from a light translucent or transparent material, such that any suitable light may be shined through the at least one wall thereof. An upper perimeter of the container portion is treated, such that light will not shine through an upper twenty five percent of the container by volume. An opaque tape, an opaque paint, an opaque printing ink or any other suitable treatment is applied to an upper perimeter of the container portion to prevent light from passing through the container portion. At least one wall of the container is treated.

12 Claims, 5 Drawing Sheets

SHARPS CONTAINER WITH BLACKOUT STRIP

BACKGROUND OF THE INVENTION

1. Field of the Invention

The present invention relates generally to the destruction of medical waste and more specifically to a sharps container with blackout strip to prevent overfilling of a container portion.

2. Discussion of the Prior Art

The problems associated with the destruction and decontamination of medical waste are well-known. Syringes, plastic blood bags, metal clips, hoses, etc. present formidable problems for disposal. Not only are they difficult to deal with due to safety risks to handlers and health compliance regulations, but also, they are contaminated with viral and bacterial pathogens, which make their handling hazardous. These items must be decontaminated, rendered harmless and disposed of to prevent the transmission of disease, and to avoid accessibility of used needles and syringes, stick injuries, and for purposes of general sanitation.

Devices adapted for the disposal of hospital waste are known. However, they suffer from a number of limitations, such as safety problems, including leaks and other shortcomings, which make them not particularly suitable to institutional applications where relatively unskilled workers are employed as operators. Moreover, since these devices are employed for the disposal of glass, plastic and other implements, the wear and tear on the devices is considerable. The users are generally incapable of keeping the devices in proper ranges and condition as well as within storage and filling requirements to avoid damage. They thus require either the presence of a skilled medical waste handler on staff or frequent calls to a medical waste handler.

Since the advent of the disposal syringe and other disposable medical articles, there has also arisen a need for a method to prevent their misuse and theft. In hospitals today there is a tremendous volume of these articles, which after being used, must be accounted for by some method or another, all of which takes precious time. There is an ever-growing problem with theft of used syringes for illegal intra-venous drug use and/or for drug diversion.

Typically, syringes and needles are simply thrown into sharps containers and stored until the containers are collected by waste processing and disposal personnel of a facility. Storage of whole syringes and needles also pose safety risks for waste disposal collection personnel and stick injuries during collection as often times the containers are overfilled. There exists the possibility of containers breaking and collection personnel accidentally getting stuck with contaminated needles. The United Nations has identified this problem as a world-wide health issue and set guidelines regarding the filling of sharps containers.

A sharps container is attached to a wall and can be found in almost every hospital room, clinic and nursing home as well as public places. Federal and United Nations world-wide guidelines require that a sharps container cannot be filled to more than three quarters of its volume. The sharps container is positioned between a light emitter and a light receiver inside of a cabinet or storage device. The area where sharps container is placed must be cleaned from time to time. The cleaning may change a height of the light emitter and light receiver and depending on container size.

Sharps containers are overfilled because nothing currently stops this from occurring. Containers for 510K clearance from the FDA are to have a fill line for the customers either in the plastic or on the label but no mechanism to stop overfilling. Additionally, it the customer fills to the ¾ line then it requires them to spend more on another container costing more money and for medical waste pickup, which is also an additional cost so really no incentive to not overfill.

A user of the sharp's container may want to cheat and fill the volume of the sharp's container to more than three quarters to save money on containers, disinfection and disposal. Finally, different heights of sharps containers require the light emitter and receiver to be adjusted. If the adjustment is too high, more than three quarters of the sharp's container will be filled.

Accordingly, there is a clearly felt need in the art to provide a sharp's container with blackout strip to prevent overfilling of the sharp's container, due to a light emitter being improperly adjusted or a user wanting to overfill to save costs.

SUMMARY OF THE INVENTION

The present invention provides a sharp's container with blackout strip to prevent overfilling of the sharp's container. The sharp's container includes a container portion and a closeable lid. The sharp's container includes any suitable cross-sectional shape having at least one wall. The container portion is fabricated from a light translucent or transparent material, such that any suitable light may be shined through the at least one wall thereof.

An upper perimeter of the container portion is treated, such that light will not shine through an upper twenty five percent of the container portion by volume. An opaque tape, an opaque paint, an opaque plastic, an opaque printing ink or any other suitable opaque treatment is preferably applied to the outer perimeter of the container portion to prevent light from passing through the container portion. At least one wall of the container is treated. The opaque treatment could also be applied to an upper inner perimeter of the container portion.

Accordingly, it is an object of the present invention to provide a sharp's container with blackout strip to prevent overfilling of the container portion, due to a light emitter being improperly adjusted, or a user wanting to overfill to save costs.

These and additional objects, advantages, features and benefits of the present invention will become apparent from the following specification.

DETAILED DESCRIPTION OF THE PREFERRED EMBODIMENTS

Figure 1:
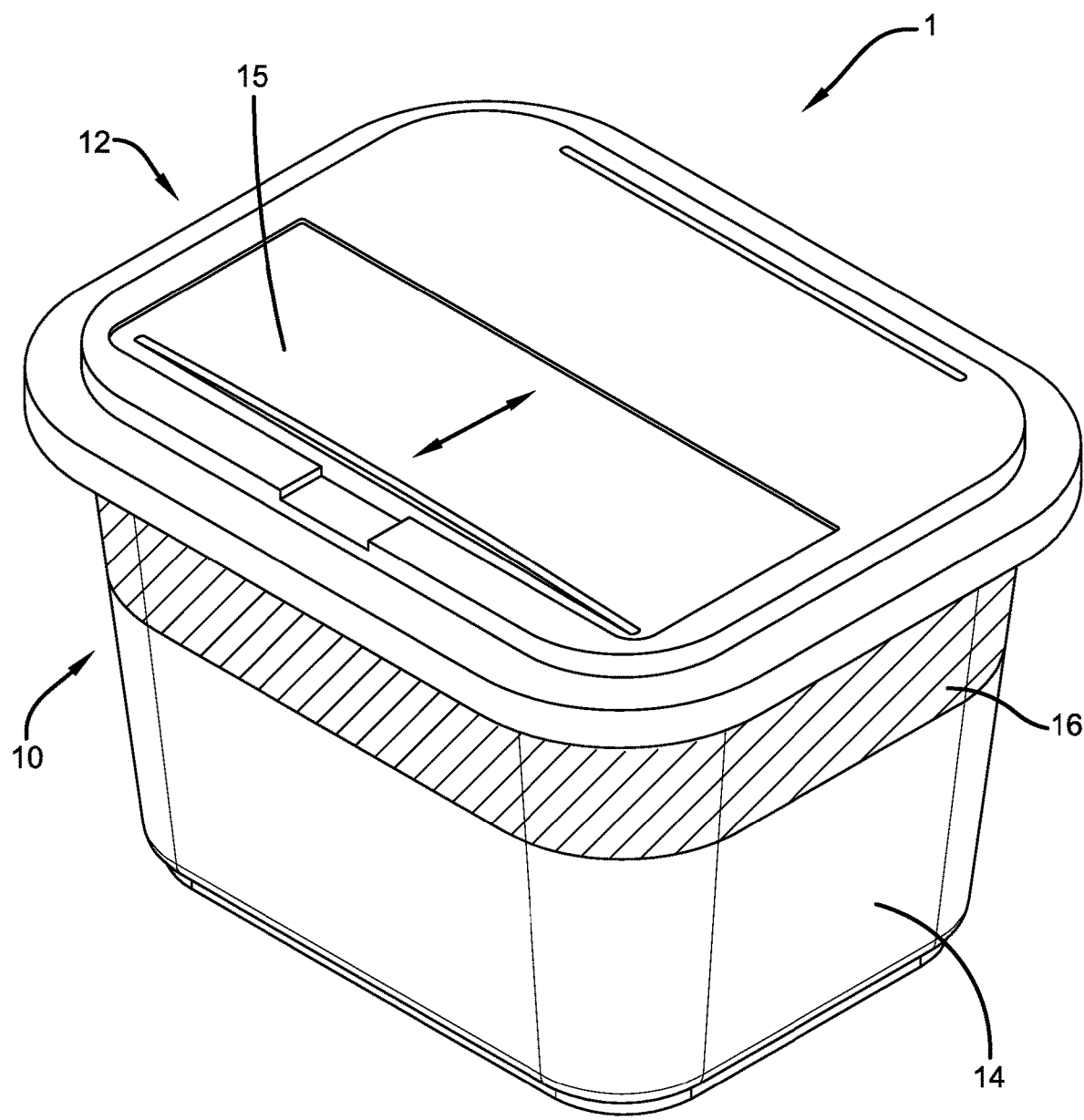
FIG. 1 is perspective view of a sharp's container with a blackout strip applied to upper perimeter in accordance with the present invention.
Figure 2:
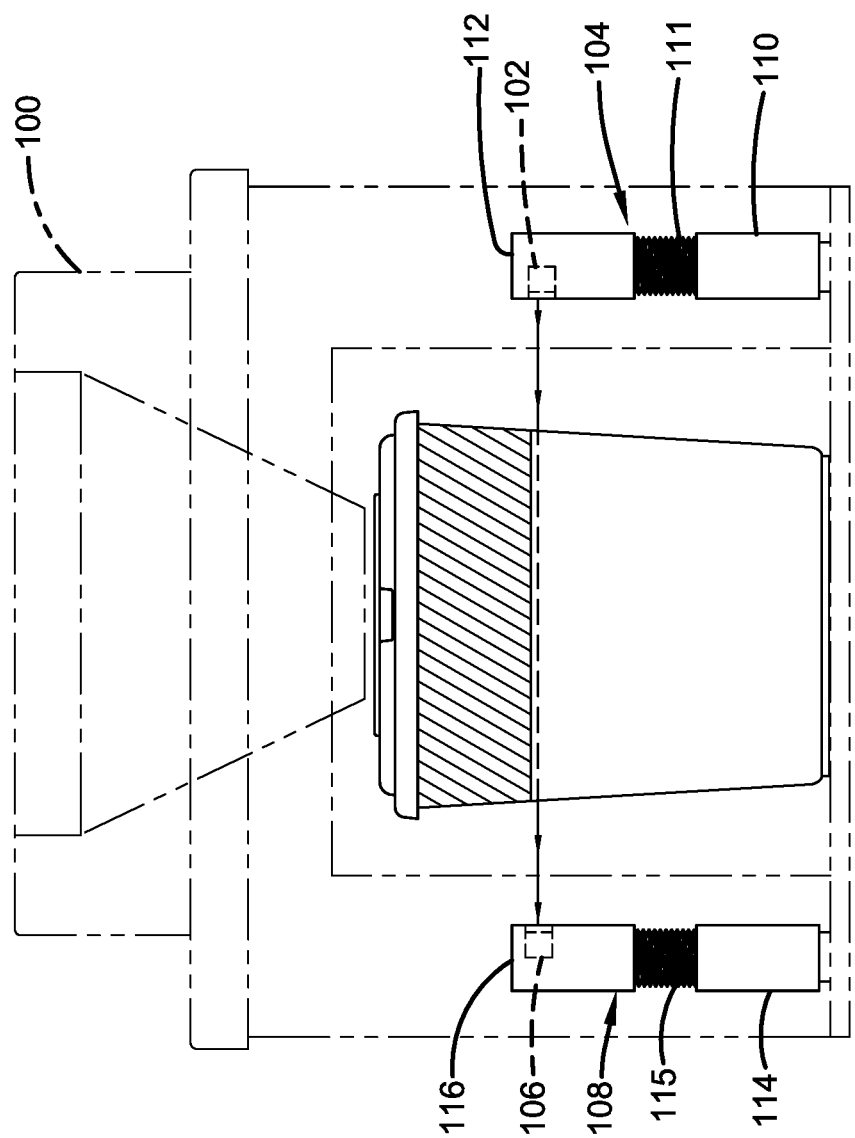
FIG. 2 is a front view of a sharp's container positioned between a light emitter and light receiver of a sharps housing in accordance with the present invention.
Figure 3:
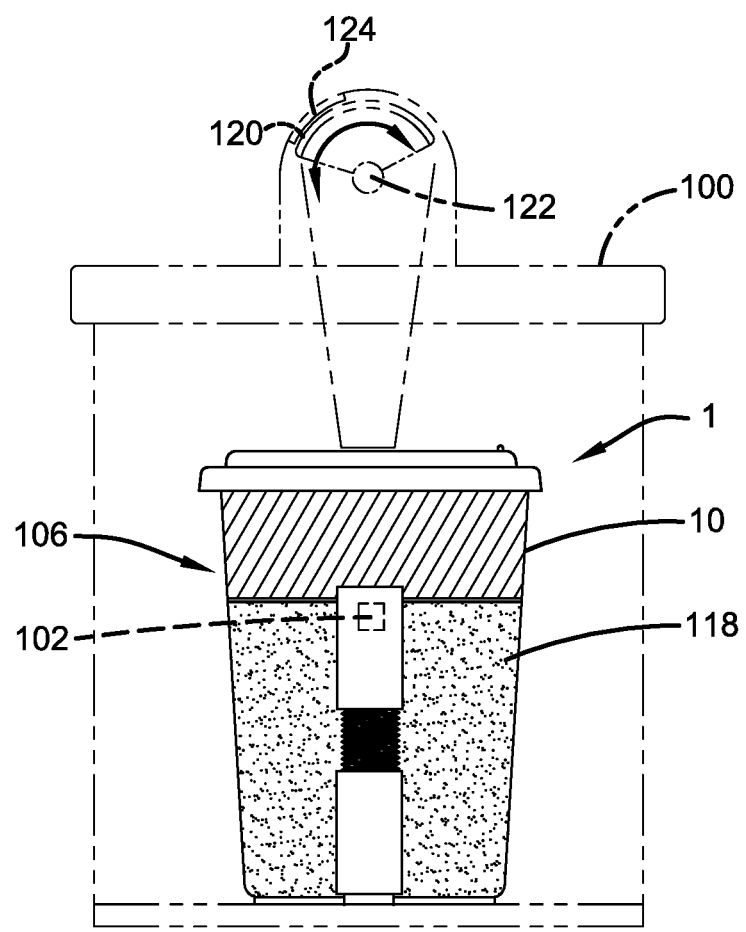
FIG. 3 is an end view of a sharps housing with a sharp's container located therein and illustrating a trap door for closing a sharps slot in a top of the sharps housing.

With reference now to the drawings, and particularly to FIG. 1, there is shown a perspective view of a sharp's container 1. The sharp's container 1 includes a container portion 10 and a closable lid 12. The closable lid 12 is retained on a top of the container portion 10. The closable lid 12 includes a sliding door 15. With reference to FIGS. 2-3, the sliding door 15 is closed, after removal from a sharps housing 100. The container portion 10 includes any suitable cross-sectional shape having at least one wall 14. The container portion 10 is fabricated from a light translucent or transparent material, such that any suitable light may be shined through the at least one wall 14.

An upper perimeter of the container portion 10 includes an opaque treatment 16, such that light will not shine through an upper twenty five percent of the container portion 10, preferably by volume. An opaque tape, an opaque paint, an opaque printing ink, an opaque plastic or any other suitable treatment is applied to preferably an outer perimeter of the sharp's container to prevent light from passing through the container portion 10. The opaque treatment 16 could also be molded into the container portion 10. At least an upper portion of only one wall 14 of the container portion 10 is treated. The opaque treatment 16 could also be applied to an inner upper perimeter of the container portion 10.

With reference to FIG. 2, a light emitter 102 is retained in a height adjustable emitter pedestal 104. A light receiver 106 is retained in a height adjustable receiver pedestal 108. The light emitter 102 and the light receiver 106 are located within a sharps housing 100. The emitter pedestal 104 includes an emitter base 110, an emitter adjustment device 111 and an emitter retainer 112. The emitter adjustment device 111 is manipulated to change a vertical height of the emitter retainer 112 relative to the emitter base 110. The receiver pedestal 108 includes a receiver base 114, a receiver adjustment device 115 and a receiver retainer 116.

The receiver adjustment device 115 is manipulated to change a vertical height of the receiver retainer 116 relative to the receiver base 114.

Figure 4:
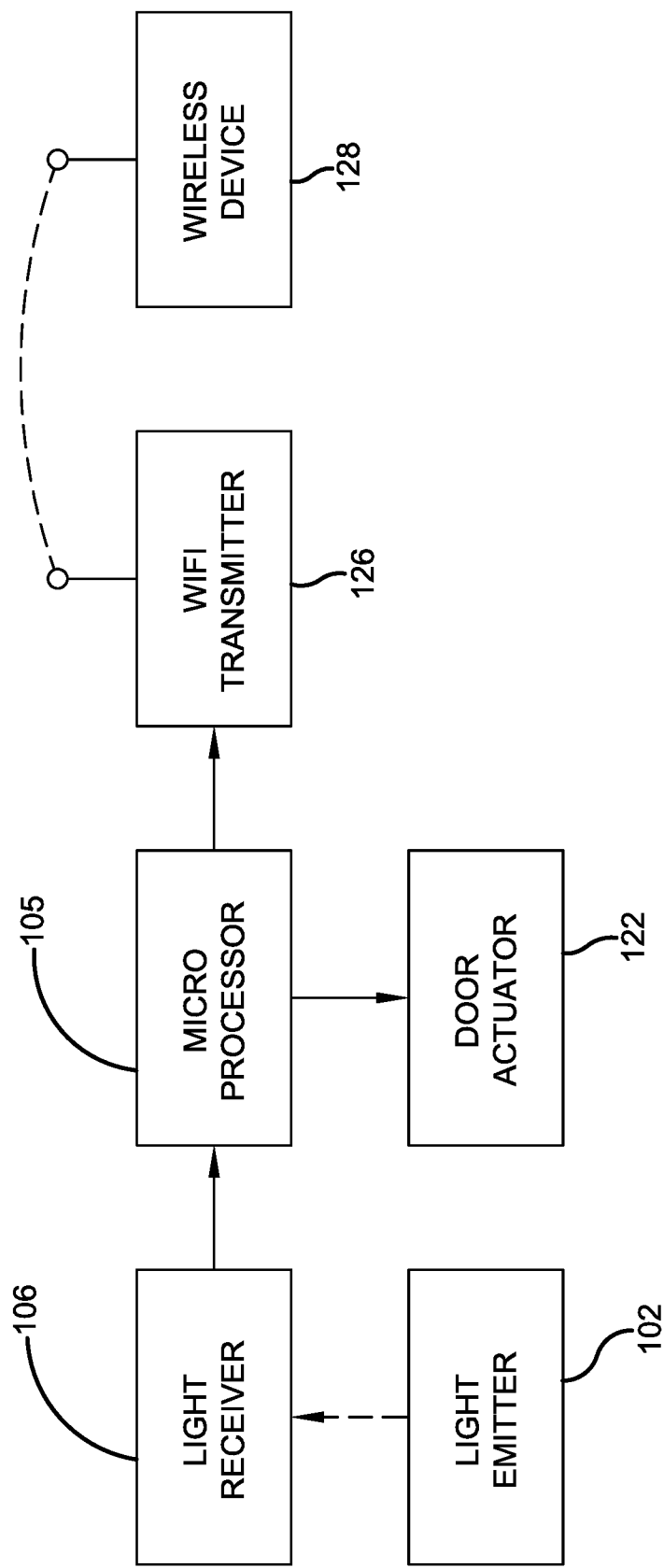
FIG. 4 is a schematic diagram of a microprocessor connected to a door actuator of a sharps housing and sending a message to a safety person to change the sharp's container driven by a Unique Device Identifier (UDI).
Figure 5:
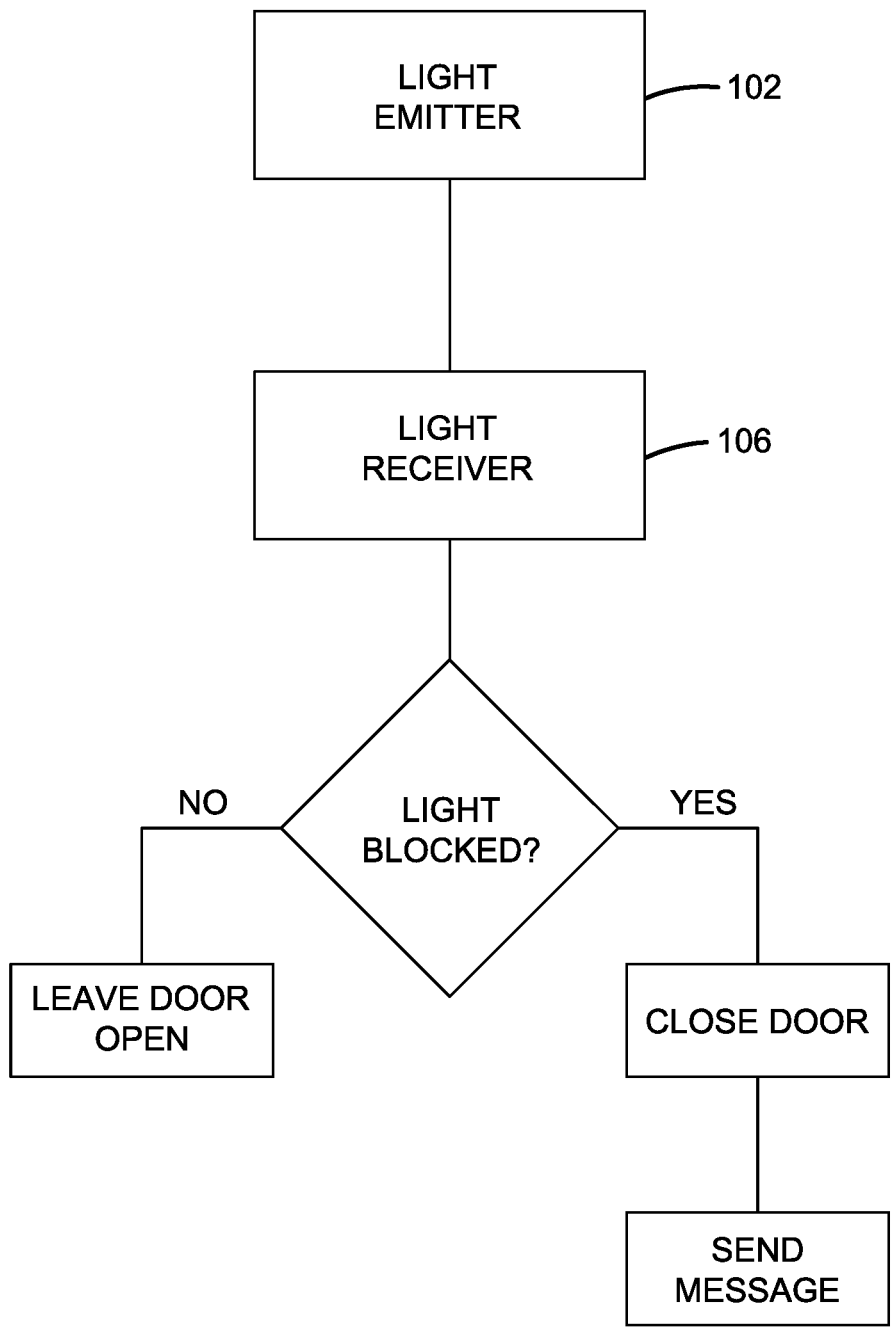
FIG. 5 is a flow chart of the operation of a light emitter, a light receiver, a microprocessor and a transmitter to detect a fill level of a sharp's container.

With reference to FIGS. 3-5, light from the light emitter 102 shines through the container portion 10 and is received by the light receiver 106. The sharps housing 100 includes a trap door 120 and a door actuator 122. The trap door 120 pivots under a sharps slot 124 formed through a top of the sharps housing 100. The trap door 120 prevents sharps from being deposited through the sharps slot 124 into a shredder device (not shown) in a top of the sharps housing 100. When the container portion 10 is filed with solid waste 118, the light from the light emitter 102 will not be received by the light receiver 106. When light is not received by the light receiver 106, the light receiver 106 sends an electrical signal to a microprocessor 105. The microprocessor 105 powers the door actuator 122 to close the trap door 102 and sends a message through a wireless transmitter 126, utilizing WiFi, RFD, or the like to a wireless device 128 or a flashing indicator light. The wireless device 128 is retained by a maintenance member. The wireless device 128 receives a message to remove a full sharp's container 1 from the sharps housing 100. A unique device identifier may be used to identify, which sharps housing 100 needs to be replaced. The maintenance member has the responsibility of removing the sharp's container 1 from the sharps housing 100 and inserting an empty sharp's container 1. If the light emitter 102 and the light receiver 106 are set too high, the opaque treatment 16 will prevent the light from being received by the light receiver 106.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A sharps container with a blackout strip, a light emitter shines light through said sharps container to a light receiver in a sharps housing, said blackout strip does not allow light to penetrate said sharps container, if the light receiver does not receive light, a trap door in the sharps housing is closed to prevent the sharps container from being filled, comprising:
    the sharps container having at least one wall, the sharps container is fabricated from a light translucent or transparent material, the blackout strip comprises a treatment applied to an upper portion of said at least one wall, said treatment does not allow light to pass through said at least one wall.

2. The sharps container with the blackout strip of claim 1 wherein:
    a closeable lid is retained on a top of the sharps container, said closeable lid includes a sliding door.

3. The sharps container with the blackout strip of claim 1 wherein:
    said treatment is an opaque tape or an opaque plastic strip.

4. The sharps container with the blackout strip of claim 1 wherein:
    said treatment is an opaque paint.

5. The sharps container with the blackout strip of claim 1 wherein:
    said treatment is an opaque ink.

6. The sharps container with the blackout strip of claim 1 wherein:
    said treatment is molded into said at least one wall.

7. A method of preventing a sharps container from being overfilled, comprising the steps of:
    retaining the sharps container in a sharps housing, the sharps housing includes a slot and a trap door, the trap door prevents sharps from being inserted through the slot into the sharps container;
    positioning the sharps container between a light emitter and a light receiver in the sharps housing; and
    providing the sharps container with at least one wall, the sharps container is fabricated from a light translucent or transparent material, a treatment is applied to an upper portion of said at least one wall, said treatment does not allow light from said light emitter to pass through said at least one wall, a signal is sent from the light receiver to close the trap door if the light receiver does not receive light from the light emitter.

8. The method of preventing the sharps container from being overfilled of claim 7, comprising the step of:
    providing a closeable lid for retention on a top of the sharps container, said closeable lid includes a sliding door.

9. The method of preventing the sharps container from being overfilled of claim 7, comprising the step of:
    providing said treatment as an opaque tape or an opaque plastic strip.

10. The method of preventing the sharps container from being overfilled of claim 7, comprising the step of:
   providing said treatment as an opaque paint.

11. The method of preventing the sharps container from being overfilled of claim 7, comprising the step of:
   providing said treatment as an opaque ink.

12. The sharps container with the blackout strip of claim 7 wherein:
   providing said treatment as molded into said at least one wall.

\* \* \* \* \*